United States Patent [19]

Sangokoya

[11] Patent Number: 5,099,050

[45] Date of Patent: Mar. 24, 1992

[54] PREPARATION OF ALUMINOXANES

[75] Inventor: Samuel A. Sangokoya, Baton Rouge, La.

[73] Assignee: Ethyl Corporation, Richmond, Va.

[21] Appl. No.: 684,810

[22] Filed: Apr. 15, 1991

[51] Int. Cl.$^5$ ................................................ C07F 5/06
[52] U.S. Cl. ...................................... 556/179; 556/182
[58] Field of Search ................................. 556/179, 182

[56] References Cited

U.S. PATENT DOCUMENTS

| | | | |
|---|---|---|---|
| 3,219,591 | 11/1965 | Vandenberg | 252/431 |
| 4,404,344 | 9/1983 | Sinn et al. | 526/160 |
| 4,544,762 | 10/1985 | Kaminsky et al. | 556/179 |
| 4,665,208 | 5/1987 | Welborn et al. | 556/179 |
| 4,730,071 | 3/1988 | Schoenthal et al. | 556/179 |
| 4,730,072 | 3/1988 | Schoenthal et al. | 556/179 |
| 4,772,736 | 9/1988 | Edwards et al. | 556/179 |

FOREIGN PATENT DOCUMENTS

| | | |
|---|---|---|
| 208561 | 1/1987 | European Pat. Off. . |
| 315234 | 5/1989 | European Pat. Off. . |
| 3240383 | 3/1984 | Fed. Rep. of Germany . |
| 63-87717 | 7/1988 | Japan . |

*Primary Examiner*—Jose G. Dees
*Assistant Examiner*—Porfirio Nazario
*Attorney, Agent, or Firm*—David M. Bunnell

[57] ABSTRACT

Hydrocarbyl aluminoxanes such as methylaluminoxanes are preapred by reacting a hydrocarbylaluminum compound with a hydrate of an alkali metal halide.

14 Claims, No Drawings

PREPARATION OF ALUMINOXANES

BACKGROUND

This invention relates generally to a process for preparing aluminoxanes and more specifically to the preparation of aluminoxanes, such as methylaluminoxane, by reacting a hydrocarbyl aluminum compound with a hydrate of an alkali metal halide such as lithium bromide dihydrate.

Vandenberg U.S. Pat. No. 3,219,591 reported the catalytic activity of compounds formed by the reaction of trialkyl aluminum with limited amounts of water in the polymerization of epichlorohydrin and other oxiranes. Shortly thereafter, Manyik, et al. U.S. Pat. No. 3,242,099 reported the use of aluminoxanes, made by reacting 0.85-1.05 moles of water with hydrocarbyl aluminum compounds such as triisobutylaluminum, as co-catalysts with certain transition metal compounds in the polymerization of monounsaturated α-olefins; e.g. ethylene and propylene. Isobutylaluminoxane was also made by adding an equal mole quantity of water to a heptane solution of triisobutylaluminum.

Manyik, et al. U.S. Pat. No. 3,300,458 prepare alkylaluminoxane by passing a hydrocarbon through water to form a wet hydrocarbon and mixing the wet hydrocarbon and an alkyl aluminum/hydrocarbon solution in a conduit.

Schoenthal, et al. U.S. Pat. No. 4,730,071 show the preparation of methylaluminoxane by dispersing water in toluene using an ultrasonic bath to cause the dispersion and then adding a toluene solution of trimethylaluminum to the dispersion. Schoenthal, et al. U.S. Pat. No. 4,730,072 is similar except it uses a high speed, high shear-inducing impeller to form the water dispersion.

Edwards, et al. U.S. Pat. No. 4,722,736 describe an aluminoxane process in which water is introduced below the surface of a solution of hydrocarbyl aluminum adjacent to a stirrer which serves to immediately disperse the water in the hydrocarbon solution.

The preparation of alkyl aluminoxanes from $R_2AlOLi$, formed by reacting $AlR_3$ and anhydrous lithium hydroxide, and $R_2AlCl$ has been reported in the literature, for example, Ueyama, et al., Inorganic Chemistry, 12, No. 10, 2218 (1972) and Aoyazi, et al., Inorganic Chemistry, 12, No. 11, 2702 (1973).

Sinn, et al. U.S. Pat. No. 4,404,344 prepare methylaluminoxane by adding trimethylaluminum to a slurry of $CuSCO_4 \cdot 5H_2O$ in toluene. Introducing water as a metal hydrate controls its reactivity with the trimethylaluminum. Kaminsky, et al. U.S. Pat. No. 4,544,762 is similar except it uses an aluminum sulfate salt hydrate to supply the water. Likewise, Welborn, et al. U.S. Pat. No. 4,665,208 describe the use of other metal salt hydrates such as $FeSO_4 \cdot 7H_2O$ as a water source in preparing aluminoxane. Kioka, et al. Japanese Patent Application 63-87717 discloses the use of hydrate salts which contain water of absorption or crystallization such as hydrated magnesium chloride, hydrated copper sulfate, hydrated ammonium sulfate, hydrated nickel sulfate and hydrated cerium III chloride.

A process has now been discovered for making hydrocarbylaluminoxanes using certain halide salt hydrates which greatly improves the recovery of aluminum values by permitting the use of lower reaction temperatures. Also, gel formation in aromatic solvents is avoided when preparing aluminoxanes from hydrocarbyl aluminum compounds where the alkyl groups have 2 or more carbon atoms, such as triethylaluminum, and triisobutylaluminum such that the products are easily filtered.

SUMMARY OF THE INVENTION

In accordance with this invention, there is provided a process for preparing a hydrocarbylaluminoxane comprising reacting a hydrocarbylaluminum compound with a hydrate of an alkali metal halide.

DETAILED DESCRIPTION

Hydrocarbylaluminoxanes may exist in the form of linear or cyclic polymers with the simplest compounds being a tetraalkylaluminoxane such as tetramethylaluminoxane, $(CH_3)_2AlOAl(CH_3)_2$, or tetraethylaluminoxane, $(C_2H_5)_2ALOAl(C_2H_5)_2$. The compounds preferred for use in olefin polymerization catalysts usually contain about 4 to 20 of the repeating units:

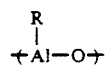

where R is $C_1$-$C_8$ alkyl.

The hydrates which are useful in the invention include hydrates of alkali metal halides such as, for example, lithium, sodium and potassium hydrates. These compounds can form hydrates which readily lose water which permits the reaction to be carried out at room temperature or below. For example, sodium bromide dihydrate, potassium fluoride dihydrate, lithium bromide dihydrate, lithium chloride monohydrate and lithium iodide trihydrate and the like, including mixtures thereof.

Any hydrocarbyl aluminum compound capable of reacting with the hydrate to form an aluminoxane can be used. This includes, for example, trialkyl aluminum, triaryl aluminum, mixed alkyl aryl aluminum, and the like.

The preferred aluminum compounds are the alkyl aluminum compounds, especially trialkyl aluminum compounds such as trimethylaluminum, triethylaluminum, triisobutylaluminum, tri-n-hexylaluminum, trioctylaluminum and the like. Of these, the more preferred are the tri-$C_{(1-4)}$-alkylaluminum compounds.

Of the various hydrocarbyl aluminoxanes, methylaluminoxane and ethylaluminoxane are the more difficult to prepare because of the extreme reactivity of trimethylaluminum and triethylaluminum with water. The most reactive is trimethylaluminum and accordingly the most preferred embodiment is the application of the process to make methylaluminoxane.

Methylaluminoxanes prepared by direct water addition are only sparingly soluble in toluene. Furthermore, on standing, formation of gelatinous viscous material usually accompanies concentrated solutions thus prepared. Methylaluminoxanes prepared by the alkali metal halide hydrate method of the invention are essentially gel-free even at concentrations of 15-25 weight percent aluminum.

The reaction is carried out in an inert solvent. Any inert solvent can be used. The preferred solvents are aliphatic and aromatic hydrocarbons. Aromatic hydrocarbons are more preferred such as toluene, xylene, ethylbenzene, cumene, mesitylene and the like. The most preferred solvent is toluene.

The concentration of the hydrocarbyl aluminum compound in the inert solvent can range from about 1–30 weight percent. A preferred concentration is about 5–20 weight percent, more preferably 10–15 weight percent.

The mole ratio of aluminum compound to water in the alkali metal halide hydrate can vary widely such as, for example, from about 2:1 to 1:4 with ratios of from about 4:3 to 1:3.5 being preferred.

Unlike the reactions of prior art salt hydrates which require heating to temperatures of 70° C. or more, and usually are accompanied by a 40 to 60 percent loss of aluminum values, the process of the invention can be carried out at room temperature or below. This reduces the loss of aluminum values to as low as 2 to 5 percent. The minimum temperature is that at which the reaction will proceed and the maximum temperature is selected to optimize the yield of aluminoxane without excessive loss of aluminum values. Suitable temperatures range, for example, from about $-20°$ C. to 60° C. with $-5°$ C. to 40° C. being preferred where the higher temperature is only due to the exothermicity of the reaction and not due to any external heat. Representative reaction times depend upon the reaction temperature and aluminum alkyl concentration, for example, typically from 1 to 20 hours or more. The products are readily filtered and the salts can be recovered for regeneration of the hydrate for re-use and do not react with the aluminoxane product such that the product is not degraded even when long reaction times are used.

The process produces high yield of soluble hydrocarbylaluminoxane which has good selective activity as a catalyst component for olefin polymerization.

The invention is further illustrated by, but is not intended to be limited to, the following examples. All experiments were carried out under inert atmosphere conditions, using Schlenk glassware and vacuum line, in conjunction with a $N_2$-dry box. Solvents were dried using standard methods. Filtration and vacuum distillation were done inside the $N_2$ dry box and distillates collected in a trap at $-78°$ C.

EXAMPLE 1

Trimethylaluminum (TMA) (15.0 g, 0.20 mol) was dissolved in toluene (200.0 mL). At room temperature, $LiBr \cdot 2H_2O$ (12.7 g, 0.10 mol) was slowly added in small batches during a period of about one hour. The reaction temperature rose quickly to 38° C. and then started to cool down. The mixture was stirred for a total reaction time of about 4 hours. The slurry was filtered and the residue washed with toluene. The clear filtrate and washings were combined and analyzed for soluble aluminum content. The solution (201 g) was found to contain 2.25 weight percent aluminum which is equivalent to 84 percent of the initial aluminum content.

EXAMPLE 2

$LiBr \cdot 2H_2O$ (19.2 g, 0.16 mol) was suspended in toluene (200 mL) in a 3-neck flask equipped with a condenser, mechanical stirrer and an addition funnel. The solution was cooled to $-20°$ C. and TMA (15 g, 0.10 mol) was slowly added. After addition, cooling was stopped and the mixture slowly warmed to 20° C. Total reaction time was 2 hours. The mixture was filtered and the residue washed with toluene. Analysis of combined washings and filtrate indicated about 98 percent recovery of the initial aluminum value. This example showed that low temperature and stirring resulted in a significant improvement in the percentage of recovered aluminum value.

EXAMPLE 3

TMA was again hydrolyzed with $LiBr \cdot 2H_2O$. The reaction was carried out as described in Example 2. Total reaction time was 4 hours. The resulting clear, gel-free solution contained 95 percent of the original aluminum value.

EXAMPLE 4

TMA (15 g, 0.20 mol) was dissolved in toluene (400 mL). $LiCl \cdot 1H_2O$ (9.4 g, 0.16 mol) was slowly added via a funnel, in small batches, during a period of about one hour. The reaction temperature rose to 37° C. and then started to fall after about 2.5 hours. Total reaction time was about 3.5 hours. The mixture was filtered and the residue was washed with toluene. Recovered aluminum value was about 85 percent of the initial value.

EXAMPLE 5

This reaction was carried out as described for Example 4 above, except that the mole ratio $TMA/LiCl \cdot 1H_2O$ was 1:1 instead of 4:3. The temperature rose to 38° C. and then started to drop. Total reaction time was 3 hours. The percentage of aluminum recovered was 75 percent of the initial aluminum value.

EXAMPLE 6

TMA (15 g, 0.20 mol) was dissolved in toluene (400 mL). $LiI \cdot 2H_2O$ (13.2 g, 0.08 mol) was slowly added to the TMA solution at room temperature. The solid was added such that the reaction temperature was kept below 32° C. Total reaction time was 3.5 hours. The mixture was filtered and the residue washed with toluene. The combined washings and filtrate (365 g) contained 1.1 weight percent aluminum which is equivalent to about 72 percent of the initial aluminum value.

EXAMPLE 7

A 4:3 mole ratio ($TMA/H_2O$) reaction at room temperature using a magnetic stirrer was carried out by first dissolving TMA (15 g, 0.2 mol) in toluene (400 mL). Then, $LiBr \cdot 2H_2O$ (9.5 g, 0.07 mol) was added in small batches during a period of about 1.5 hours. The reaction temperature was kept below 32° C. during addition by controlling the amount of solid added. At the end of addition, the reaction temperature rose to 35° C. Total reaction time was 3.5 hours. The product was worked up as described above. Eighty percent of the initial aluminum value was recovered.

EXAMPLE 8

$LiBr \cdot 2H_2O$ (7.3 g, 0.06 mol) was added in small portions, at room temperature, to toluene (400 mL) solution of triisobutyl-aluminum (TIBA) (23.5 g, 0.12 mol). The reaction temperature rose to 60° C. and then started to cool down. Total reaction time was 2 hours. The mixture was filtered and the residue washed with toluene. Clear colorless and gel-free product resulted. Furthermore, no TIBA was detected by pyridine titration. This experiment showed that fully hydrolyzed IBAO could be produced in toluene solution using $LiBr \cdot 2H_2O$.

EXAMPLE 9

The reaction as described in Example 8 was repeated using heptane instead of toluene. A clear, colorless gel-free solution product was obtained. Recovered aluminum value was 78 percent.

The main use of alkylaluminumoxanes is as a cocatalyst with a transitional metal compound in the polymerization of olefins to make syndiotactic polymers. Chemical analysis of various alkylaluminoxanes can be very similar even when the catalytic activity of the products differ greatly. For this reason the products are preferably evaluated using a polymerization test. One such test involves the polymerization of ethylene under pressure in dry toluene containing methylaluminoxane (MAO) and a zirconium compound. The amount of MAO, zirconium compound and ethylene is the same in each test. After the polymerization is complete, the polyethylene is recovered, dried and weighed. The test criteria is the amount of polyethylene formed from which a specific activity can be calculated.

Methylaluminoxane prepared according to Example 1 was used in the polymerization of ethylene. The specific activity in gPE/mol Zr·atm·hr was $3766 \times 10^6$.

Methylaluminoxane prepared according to Example 2 was used in the polymerization of ethylene. The specific activity in gPE/mol Zr·atm·hr was $4483 \times 10^6$.

Methylaluminoxane prepared according to Example 5 was also employed in the polymerization of ethylene. The specific activity in gPE/mol Zr·atm·hr was $3542 \times 10^6$.

What is claimed is:

1. A process for preparing methylaluminoxane comprising reacting a solution of trimethylaluminum in an inert hydrocarbon solvent with an alkali metal halide hydrate selected from lithium bromide dihydrate, lithium chloride monohydrate, lithium iodide dihydrate, lithium iodide trihydrate, potassium fluoride dihydrate, and sodium bromide dihydrate, including mixtures thereof.

2. The process of claim 1 wherein said alkali metal halide hydrate is $LiCl·1H_2O$, $LiBr·2H_2O$, or $LiI·2H_2O$.

3. The process of claim 1 wherein the reaction temperature is from about $-20°$ C. to $60°$ C.

4. The process of claim 1 wherein the mole ratio of trimethylaluminum to water in the hydrate is from about 2:1 to 1:4.

5. The process of claim 4 wherein the mole ratio of trimethylaluminum to water in the hydrate is from about 4:3 to 1:3.5.

6. The process of claim 4 wherein the mole ratio of trimethylaluminum to water in the hydrate is about 1:1.

7. A process for preparing a hydrocarbylaluminoxane comprising reacting a hydrocarbylaluminum compound with a hydrate of an alkali metal halide.

8. A process of claim 7 wherein the hydrate is a lithium halide hydrate.

9. The process of claim 7 wherein the reaction temperature is from about $-20°$ C. to $60°$ C.

10. The process of claim 7 wherein the mole ratio of hydrocarbylaluminum to water in the hydrate is from about 2:1 to 1:4.

11. The process of claim 10 wherein the mole ratio of hydrocarbylaluminum to water in the hydrate is from about 4:3 to 1:3.5.

12. The process of claim 10 wherein the mole ratio of hydrocarbylaluminum to water in the hydrate is about 1:1.

13. The process of claim 7 wherein the hydrocarbylaluminum compound is trimethylaluminum.

14. The process of claim 7 wherein the hydrocarbylaluminum compound is triisobutylaluminum.

* * * * *